US009650626B2

(12) United States Patent
Takahashi et al.

(10) Patent No.: US 9,650,626 B2
(45) Date of Patent: May 16, 2017

(54) KIT FOR NUCLEIC ACID EXTRACTION AND A NUCLEIC ACID EXTRACTOR

(71) Applicant: Hitachi High-Technologies Corporation, Tokyo (JP)

(72) Inventors: Makiko Takahashi, Tokyo (JP); Kohshi Maeda, Tokyo (JP); Yasunori Shoji, Tokyo (JP); Muneo Maeshima, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 208 days.

(21) Appl. No.: 14/412,971

(22) PCT Filed: Jun. 21, 2013

(86) PCT No.: PCT/JP2013/067021
§ 371 (c)(1),
(2) Date: Jan. 5, 2015

(87) PCT Pub. No.: WO2014/007074
PCT Pub. Date: Jan. 9, 2014

(65) Prior Publication Data
US 2015/0225714 A1    Aug. 13, 2015

(30) Foreign Application Priority Data
Jul. 6, 2012    (JP) .................................. 2012-151992

(51) Int. Cl.
*G01N 1/02*    (2006.01)
*C12N 15/10*    (2006.01)
*C12Q 1/68*    (2006.01)

(52) U.S. Cl.
CPC ....... *C12N 15/1013* (2013.01); *C12Q 1/6806* (2013.01)

(58) Field of Classification Search
CPC ................... C12N 15/1013; G01N 35/0098
(Continued)

(56) References Cited

U.S. PATENT DOCUMENTS 5,837,144 A    11/1998    Bienhaus et al.
6,764,859 B1    7/2004    Kreuwel et al.
(Continued)

FOREIGN PATENT DOCUMENTS

DE    102009021201 A1    11/2010
JP    8-29425 A    2/1996
(Continued)

OTHER PUBLICATIONS

Boom et al.; "Rapid and Simple Method for Purification of Nucleic Acids"; Journal of Clinical Microbiology, Mar. 1990, pp. 495-503; vol. 28, No. 3.

*Primary Examiner* — Jan Ludlow
(74) *Attorney, Agent, or Firm* — Mattingly & Malur, PC

(57) ABSTRACT

A nucleic acid extractor reducing the possibility of cross contamination and a gene analysis apparatus having a nucleic acid amplification function and a detection function are provided. The nucleic acid extractor has a kit for nucleic acid extraction using silica-coated magnetic beads under the presence of a chaotropic agent, and includes a magnet cover 52 accommodating a magnet 42 in the inside and separating the magnet 42 and a reaction container 2, a wall part 53 covering the outside of the reaction container 2 in a state of accommodating at least a portion of the magnet cover 52 in the reaction container, and a upper portion 54 covering a space above the reaction container 2 in a state of accommodating at least a portion of the magnet cover 52 in the reaction container. Scattering of liquid and aerosol can be prevented and the possibility of cross contamination can be reduced.

15 Claims, 16 Drawing Sheets

(58) Field of Classification Search
USPC .......................................... 436/526; 422/550
See application file for complete search history.

(56) References Cited

U.S. PATENT DOCUMENTS

| | | | |
|---|---|---|---|
| 7,638,097 B2* | 12/2009 | Squirrell | B01F 15/0201 422/503 |
| 9,040,000 B2* | 5/2015 | Dinges | B01L 3/50825 374/200 |
| 2002/0141904 A1* | 10/2002 | Rosen | B01L 3/50825 422/550 |
| 2004/0029291 A1 | 2/2004 | Franzreb et al. | |
| 2008/0171337 A1 | 7/2008 | Miyazaki et al. | |
| 2010/0288705 A1 | 11/2010 | Griebel | |
| 2012/0309104 A1 | 12/2012 | Uematsu et al. | |

FOREIGN PATENT DOCUMENTS

| | | |
|---|---|---|
| JP | 2003-504195 A | 2/2003 |
| JP | 2004-524135 A | 8/2004 |
| JP | 2004-337137 A | 12/2004 |
| JP | 2008-167722 A1 | 7/2008 |
| WO | 87/05536 A1 | 9/1987 |
| WO | 2011/074456 A1 | 6/2011 |

* cited by examiner

FIG. 1
(A)
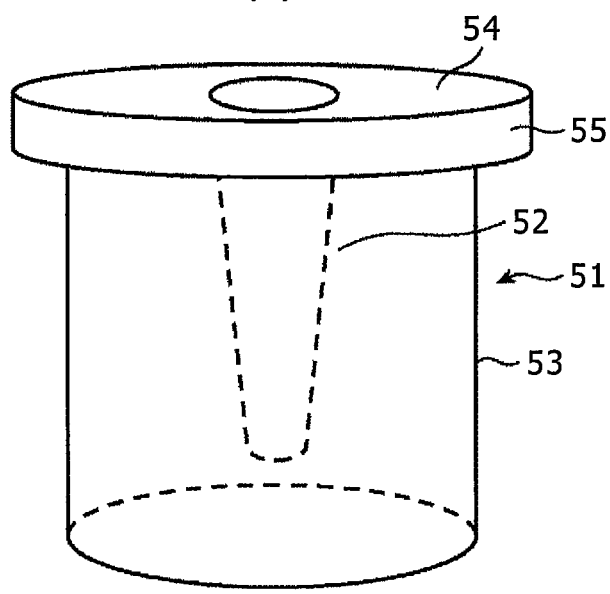
(B)
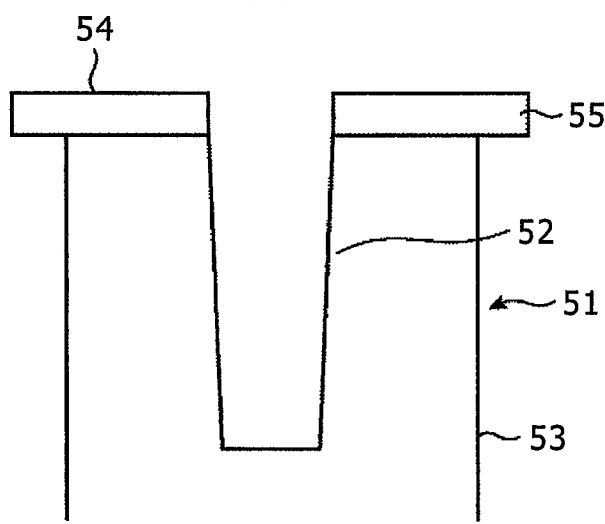

F I G . 5
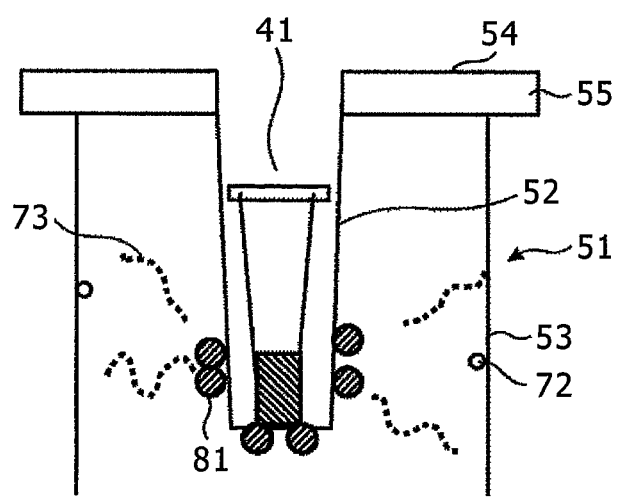

FIG.26

MOUNT NOTHING OR MOUNT MAGNETIC TIP 41 ON APICAL END OF NOZZLE 31
↓
MOVE NOZZLE 31 TO POSITION ABOVE MAGNETIC BODY COVER 51 RETAINED IN RECESS 26 OF COVER-REMOVING MECHANISM 23
↓
DOWNWARD NOZZLE 31
↓
MOUNT MAGNETIC BODY COVER 52 TO APICAL END OF NOZZLE 31
↓
MOVE NOZZLE 31 SO AS TO DETACH MAGNETIC BODY COVER 51 FROM RECESS 26 OF COVER REMOVING-MECHANISM 23 (MOVING IN Y-AXIS DIRECTION)
↓
FURTHER DOWNWARD NOZZLE 31 (DRIVING CONTROL DOWNWARDLY IN Z-AXIS DIRECTION)
↓
AGITATE SOLUTION OR CAPTURE MAGNETIC BEADS 81

FIG.27

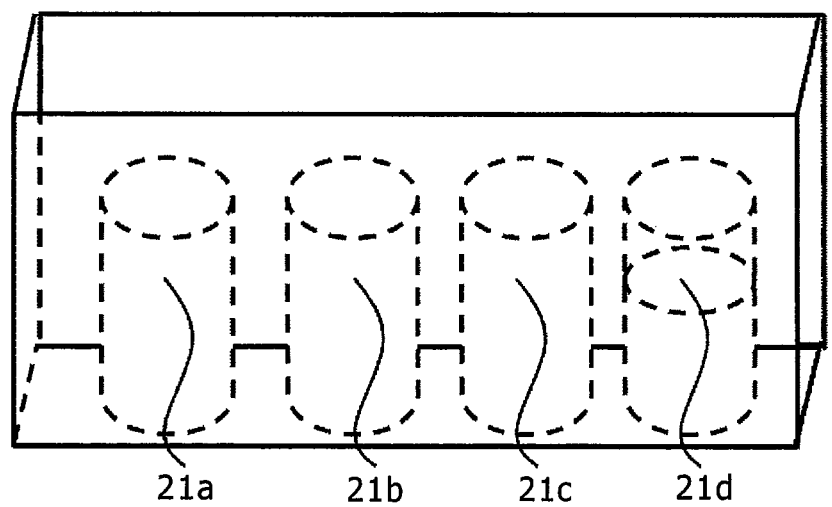

FIG. 28
(A)
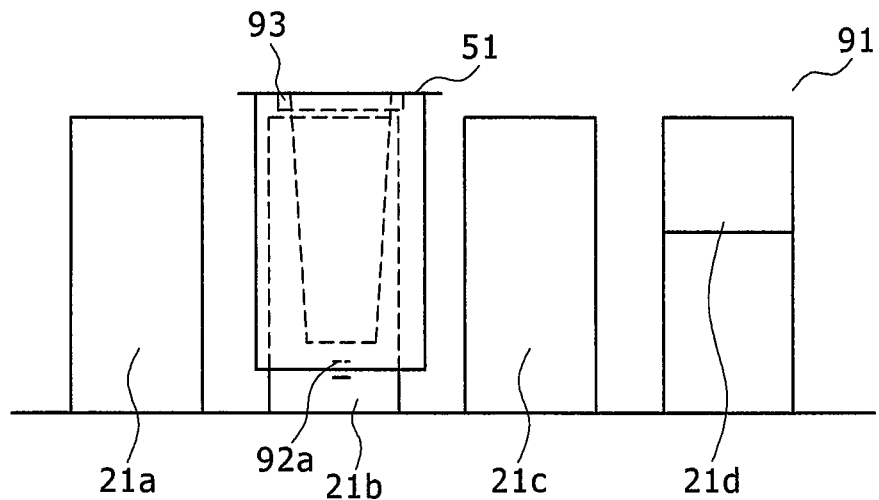
(B)
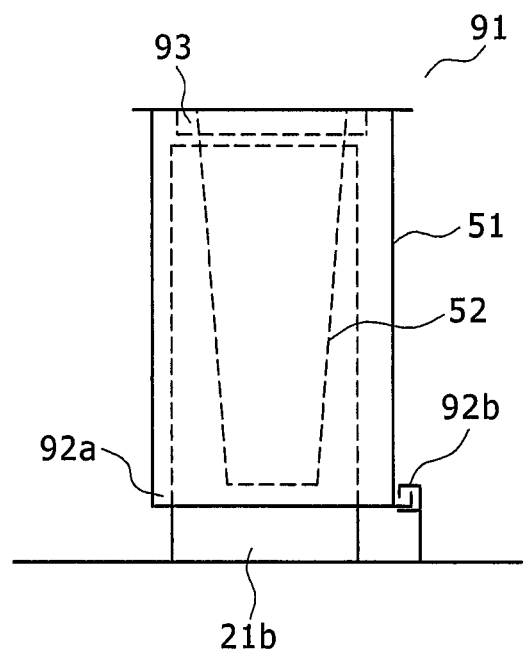

FIG.30

MOVE NOZZLE 31 ABOVE COVER RACK 6
↓
DOWNWARD NOZZLE 31 AND MOUNT MAGNETIC BODY COVER 51 OF INTEGRAL TYPE CONTAINER 91
ON APICAL END OF NOZZLE 31
↓
MOVE NOZZLE 31 ABOVE REACTION CONTAINER MOUNTING STAND 11
↓
DOWNWARD NOZZLE 31 AND DISPOSE INTEGRAL TYPE CONTAINER 91 ON REACTION CONTAINER MOUNTING STAND 11
↓
MOVE NOZZLE 31 IN X-AXIS DIRECTION. RELEASE FITTING PORTION 92a
↓
MOVE NOZZLE 31 IN Y-AXIS DIRECTION. RELEASE FITTING PORTION 92b
↓
LIFT NOZZLE 31 IN STATE OF MOUNTING MAGNETIC BODY COVER 51 (DRIVING CONTROL UPWARDLY IN Z-AXIS
DIRECTION) AND SEPARATE MAGNETIC BODY COVER 51 FROM REACTION CONTAINER 2

FIG.31

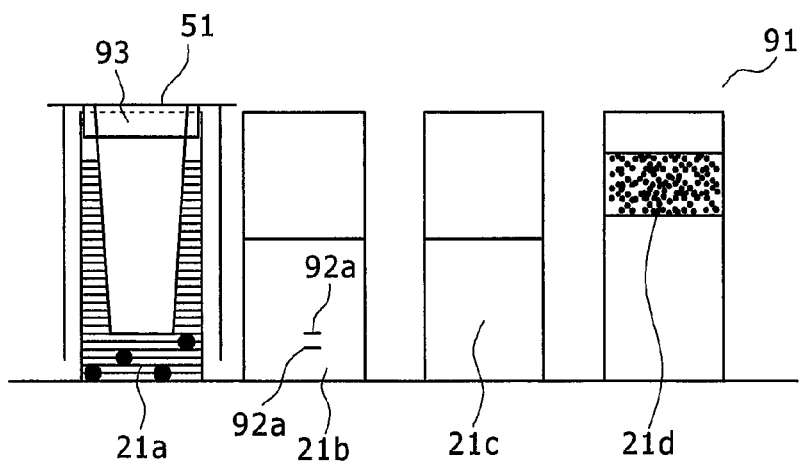

KIT FOR NUCLEIC ACID EXTRACTION AND A NUCLEIC ACID EXTRACTOR

TECHNICAL FIELD

The present invention relates to a kit for nucleic acid extraction and a nucleic acid extractor for performing various types of processing associated with extraction, separation, purification, etc. (hereinafter referred to as extraction) by using magnetic beads or magnetizable beads for processing of biological molecules such as nucleic acids (DNA or RNA) and proteins in samples containing cells, bacteria, viruses, etc.

BACKGROUND ART

Extraction of biological molecules, for example, nucleic acids from biological samples such as blood, blood plasma, and tissue fragment is a fundamental important procedure in order to obtain test substances in industries involved with diagnosis, selective plant breeding for agricultural crops, food inspection, and the like as well as for research on life phenomena such as in biological, biochemical, and medical fields. Regarding nucleic acid testing, in particular, since PCR (Polymerasechain reaction) methods capable of DNA or RNA amplification have become common, demands for extraction of purified nucleic acids that can be amplified by the PCR method are increasing. In addition to the PCR methods, various nucleic acid amplification methods such as NASBA (Nucleic Acid Sequence-Based Amplification) methods, SDA (strand displacement amplification) methods, 3CR (self-sustained sequence replication) methods, TMA (transcription-mediated amplification) methods, Qbeta replicase amplification methods, and LAMP (Loop-mediated isothermal amplification) methods have been developed. Accordingly, application range of the nucleic acid testing is extending, and it is considered that demands for extraction of nucleic acids from biological samples will increase further.

Phenol/chloroform extraction has been known as a method of extracting nucleic acids such as DNA or RNA from biological samples. This method, however, has imposed serious burdens on workers due to the use of deleterious organic solvents or complicated procedures. In order to overcome the problem described above, a method of utilizing the property of nucleic acids to bind to silica or glass fibers in the presence of a chaotropic agent was proposed (e.g., Nonpatent Literature 1), and an automatic apparatus for performing nucleic acid extraction was also developed (e.g., Patent Literature 1).

CITATION LIST

Patent Literature

Patent Literature 1: Japanese Unexamined Patent Application Publication (Translation of PCT Application) No. 2003-504195

Patent Literature 2: Japanese Unexamined Patent Application Publication No. 2004-337137

Nonpatent Literature

Nonpatent Literature 1: Boom, R., Sol, C. J. A., Salimans, M. M. M., Jansen, C. L., Wertheimvan Dillien, P. M. E., and van der Noordaa, J., J. Clin. Microbiol., 28, 495-503, (1990)

SUMMARY OF THE INVENTION

Technical Problem

The process of nucleic acid extraction carried out generally by an automatic apparatus is as described in (1) to (6) below. (1) Cells are fractured by a solution containing a chaotropic agent or a surfactant to elute nucleic acids in the solution, (2) magnetic beads coated at the surface with silica (magnetic silica particles) are added to the solution and mixed thereby allowing nucleic acids to adsorb onto the particle surface, (3) a magnet is brought closer from the outside of a reaction container, and a solution containing unnecessary substances such as proteins is removed by using a pump or the like while capturing the magnetic beads in the reaction container, (4) a cleaning solution is added to the reaction container, and unnecessary substances are allowed to migrate into the solution, (5) the magnet is again brought closer from the outside of the reaction container, and a solution containing unnecessary substances is removed while capturing the magnetic beads in the reaction container, and (6) sterilized water or low-salt buffer is added to magnetic beads after the cleaning solution has been removed to elute the nucleic acids from the magnetic bead surfaces.

A problem involved in the steps (1) to (6) is that it is difficult to completely remove the solution used for cell fracture and the cleaning solution by a liquid suction line connected to the pump or the like. Chemicals such as the chaotropic agent and the surfactant contained in the solution used for cell fracture, ethanol or isopropanol contained in the cleaning solution hinder enzymatic reactions succeeding to the PCR process or the like. Accordingly, while it is desired to remove them as much as possible, since the identical reaction container is used also after removal, there has been a problem that the residual solution may be carried to the succeeding step. Further, a problem of removing also the magnetic beads has sometimes occurred as a result of strong intention to increase the removing efficiency.

For solving the problems, there have been proposed a method of arranging magnets for capturing magnetic beads to the outside of a reaction container, a method of arranging magnets to the outside of a liquid suction pipe, a method of arranging a covered magnetic collection structure to the inside of a reaction container to capture the magnetic beads, moving the magnetic body to other reaction container, and shielding or weakening the magnetic force to transfer the magnetic beads to a new reactor container, and exchanging the solution substantially (Patent Literature 2).

Since nucleic acids extracted as testing substances from biological samples are often inspected after amplification reaction, it is required that the cross contamination between samples in the nucleic acid extraction step is as low as possible. In an existing automatic nucleic acid extracting apparatus, since the reaction container is opened and there is no shield when the magnetic beads adsorbing the sample are transported between the containers, there has been a problem that the possibility of cross contamination cannot be eliminated.

An object of the present invention is to provide a kit for nucleic acid extraction and a nucleic acid extractor that reduces the possibility of contamination of samples for nucleic acid extraction provided in one identical apparatus.

Solution to Problem

The kit for nucleic acid extraction for solving the problem is a kit for nucleic acid extraction using silica-coated magnetic beads under the presence of a chaotropic agent including a magnetic body accommodation portion for accommodating a magnetic body in the inside and separating the magnetic body and the reaction container from each other, an outer wall covering the outside of the reaction container in a state of accommodating at least a portion of the magnetic body accommodating portion in the reaction container, and a lid covering the reaction container from above in a state of accommodating at least a portion of the magnetic body accommodation portion in the reaction container.

Advantageous Effects of Invention

The kit for nucleic acid extraction according to the present invention can prevent scattering of a sample or a sample-containing liquid and aerosol near the reaction container, and reduce the possibility of contamination of samples for nucleic acid extraction provided in one identical apparatus.

BRIEF DESCRIPTION OF DRAWINGS

FIG. 1 is a perspective view and a plan view of a magnetic body cover applied with the present invention.

FIG. 5 is a schematic view of the magnetic body cover and the magnetic body tip in a case of capturing the magnetic beads.

FIG. 26 is a flow chart for the operation of implementing the procedure of mounting a magnetic body cover to the nozzle.

FIG. 27 is a perspective view of the reaction container.

FIG. 28 is a plan view in two different directions of an integral type container.

FIG. 30 is a flow chart of an operation when separating the integral type container into the reaction container and the magnetic body cover.

FIG. 31 is a plan view illustrating the integral type container in which the reaction portion is shielded by the magnetic body cover.

DESCRIPTION OF EMBODIMENTS

Figure 2:
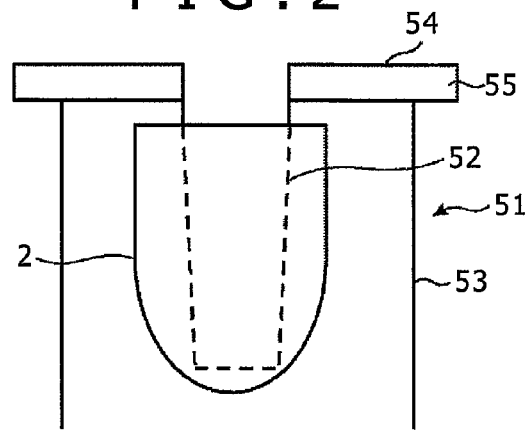
FIG. 2 is a schematic view of the magnetic body cover and a reaction container.
Figure 3:
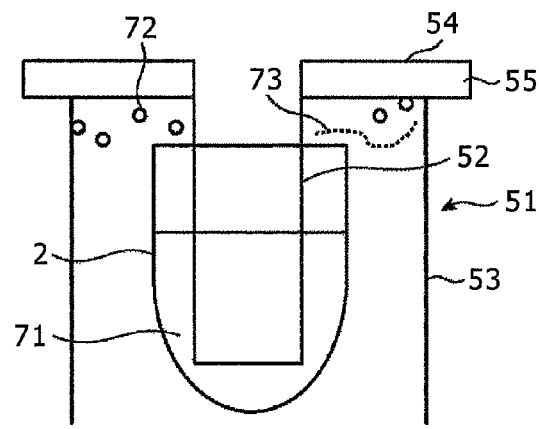
FIG. 3 is a schematic view of the magnetic body cover and the reaction container in a case where a liquid is present in the reaction container.

Hereinafter, a magnetic body cover and a nucleic acid extractor using the same, and a nucleic acid extraction method according to the present invention are described in details with reference to the drawings.

FIG. 1(A) is a perspective view (A) illustrating an embodiment of a magnetic body cover according to the present invention (kit for nucleic acid extraction) and FIG. 1(B) is a plan view thereof. A magnetic body cover 51 has a magnet cover 52 and a wall 53 which are connected at an upper portion 54. Further, the magnetic body cover 51 has a flange 55 at upper outside. The magnet cover 52 and the wall 53 define a cavity between them and can accommodate a reaction container 2 therein.

FIG. 2 schematically illustrates a state where the magnet cover 52 of the magnetic body cover 51 is present in a reaction container 2. When the magnet cover 52 of the magnetic body cover 51 is present in the reaction container 2, the reaction container 2 intrudes between the magnet cover 52 and the wall 53. With such a structure of the magnetic body cover 51 and the reaction container 2, it is possible to shield scattering of liquid droplets 72 and an aerosol 73 of a reaction solution that may possibly generate upon contact of the magnetic body cover 51 with the liquid 71 in the reaction container 2 by the wall 53 and the upper portion 54 thereby preventing contamination to adjacent sample for nucleic acid extraction. As will be described later, a plurality of reaction containers are provided in adjacent each other for nucleic acid extraction.

Figure 4:
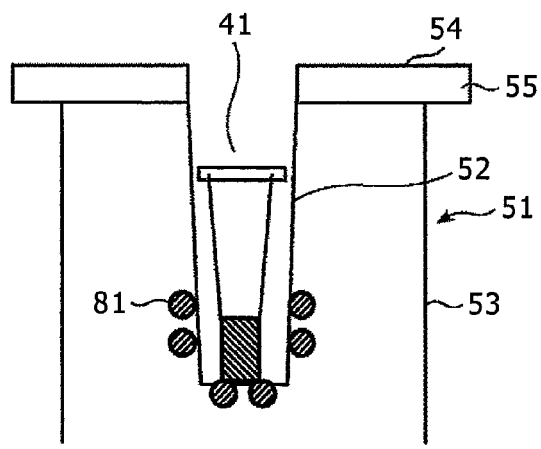
FIG. 4 is a schematic view illustrating a state where a magnetic rod is accommodated in the magnetic body cover and captures magnetic beads.

FIG. 4 schematically illustrates a case where the magnet cover 52 of the magnetic body cover 51 is present to the outside of the reaction container 2 in a state of capturing magnetic beads 81. The wall 53 of the magnetic body cover 51 has a structure longer than the length of the magnet cover 52. In the structure of such a relation of length, it is possible to shield scattering of liquid droplets 72 and aerosol 73 of a reaction solution that may possibly generate in a case where the magnet cover 52 of the magnetic body cover 51 is present outside of the reaction container 2 in a state of capturing the magnetic beads 81, thereby capable of preventing contamination to adjacent samples for nucleic acid extraction.

While FIG. 1 illustrates an example in which the magnet cover 52 and the wall 53 are connected at the upper portion 54, it may suffice that scattering of the liquid and the aerosol in the upper portion 54 of the magnetic body cover can be prevented, and the magnet cover 52 of the magnetic body cover 51 and the wall 53 may not always be an integral type.

While FIG. 1 illustrates an example in which the cross section of a magnet 42, a magnet support 45, and the magnet cover 52 are circular, cross sections of the magnet 42, the magnet support 45, and the magnet cover 52 may be a polygonal shape. Further, while FIG. 1 illustrates a case where cross sections of the magnet 42, the magnet support 45, and the magnet cover 52 are similar, they are not always restricted to a similar shape.

While FIG. 1 illustrate an example in which cross sections of the magnet 42, the magnet support 45, and the wall 53 are circular, the cross sections of the magnet 42, the magnet support 45, and the wall 53 may also be a polygonal shape. Further, while FIG. 1 illustrates a case where the cross sections of the magnet 42, the magnet support 45, and the wall 53 are similar, they are not always restricted to the similar shape.

The magnetic body cover 51 can be prepared by using a resin such as polyethylene, polypropylene, and polycarbonate.

Figure 6:
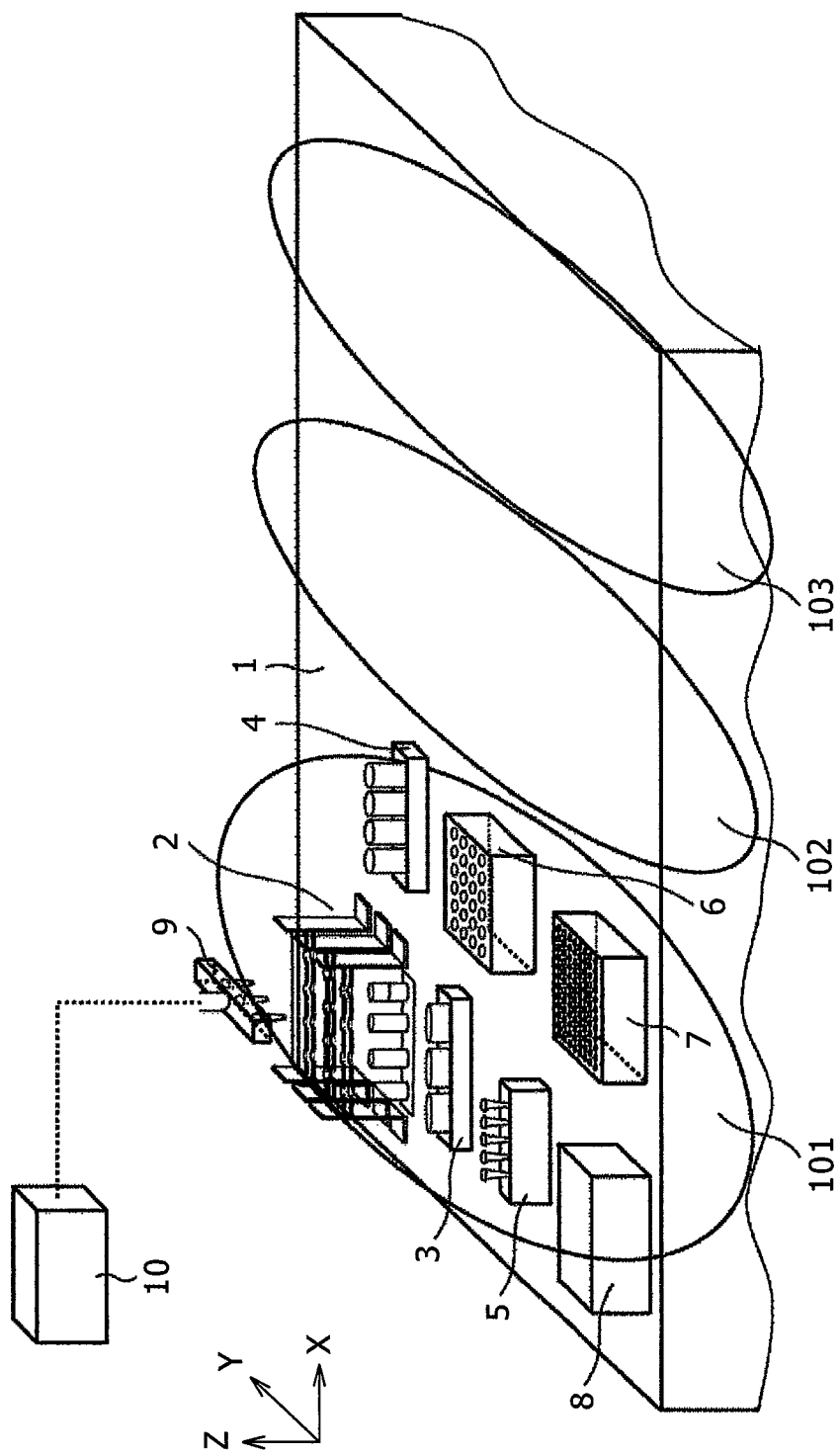
FIG. 6 is a perspective view schematically illustrating an example of an entire gene analysis apparatus according to the present invention.

Then, a nucleic acid extractor 101 having the magnetic body cover 51 according to the present invention is placed together with a nucleic acid amplification preparation portion 102 and a nucleic acid amplification reaction detection portion 103 on one surface of amounting stand as illustrated in FIG. 6.

In the nucleic acid extractor 101, various types of processing are performed for biological samples by mounting a plurality of reaction containers 2 to predetermined positions on one surface of the mounting stand 1 and using the reaction containers 2. The nucleic acid extractor includes a reagent rack 3 capable of accommodating a plurality of reagent bottles, an analyte rack 4 capable of accommodating sample containers filled with target biological samples, a magnetic rod rack 5 accommodating a plurality of magnetic rods, a cover rack 6 accommodating a plurality of magnetic body covers, a tip rack 7 accommodating a plurality of disposable tips, a waste container 8 used for discarding wastes, a nozzle mechanism 9 arranged movably at a position opposing one surface of the mounting stand 1, and a drive control device 10 for controlling movement and positioning of the nozzle mechanism 9. The nucleic acid extractor also includes a computer for inputting information regarding processing conditions, biological samples, and various other information, although not illustrated.

Biological samples, although not particularly limited herein, mean to include biological samples sampled from animals including human such as blood, blood plasma, tissue fragments, body fluids, and urine; cells such as animal cells, plant cells, and insect cells; microorganisms such as bacteria, fungi, and algae; and viruses (including virus-infected cells). Biological samples also mean to include culture solutions in which such cells, microorganisms, and viruses have been cultured and liquid suspensions obtained by suspending such cells, microorganisms, or viruses. Further, the biological samples include biological molecules that are the targets of separation, extraction, or purification implemented by the nucleic acid extractor. Biological molecules mean herein to include nucleic acids such as DNA or RNA, proteins such as enzymes or antibodies, and peptide fragments. The targets of separation, extraction, or purification implemented by the nucleic acid extractor are not limited to nucleic acids, proteins, and peptide fragments, but compounds produced from cells or microorganisms (including organic compounds or low-molecular-weight compounds) can be targets of separation, extraction, and purification as biological molecules.

Figure 7:
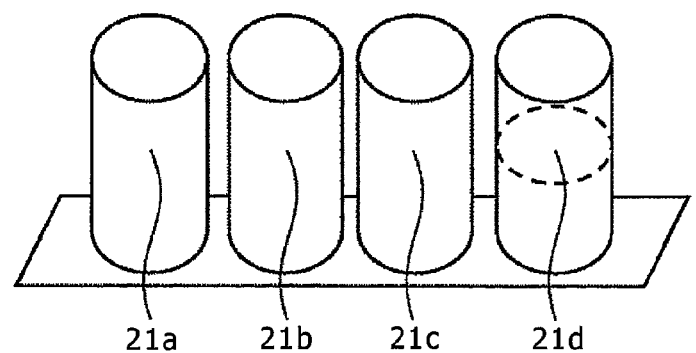
FIG. 7 is a perspective view of a reaction container.
Figure 8:
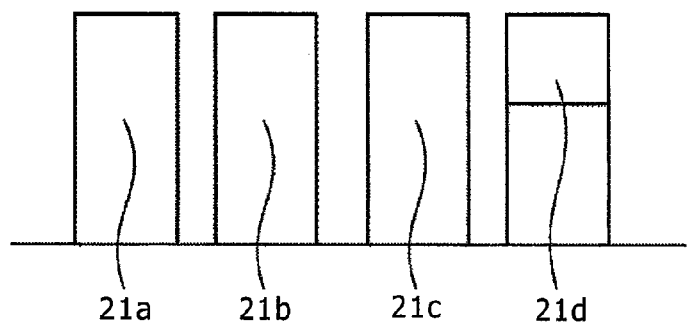
FIG. 8 is a plan view of the reaction container.

In the nucleic acid extractor, the reaction container 2 has such a configuration as illustrated in FIGS. 7 and 8 that a plurality of reaction portions 21a to 21d are arranged for dispensing various reagents. The plurality of the reaction portions 21a to 21d are provided each in a concave shape so as to provide a given volume. In this embodiment, the reaction portion 21d is formed as a shallow reaction portion that the volume of the reaction portion 21d is smaller than that of the reaction portions 21a to 21c. In the reaction container 2, the number of the reaction portions and the volume of each of the reaction portion are not particularly limited, but they can be adequately determined in accordance with the type of the processing performed on biological samples. Alternatively, in the nucleic acid extractor, reaction containers 2 of type different in the number of the reaction portions and the volume of each of the reaction portions can be mounted in accordance with the type of processing performed on biological samples.

In the reaction container 2, reaction portions 21a to 21d are surrounded with a space into which the wall 53 of the magnetic body cover 51 can intrude. The shape of the reaction container 2 provides an effect of shielding scattering of the liquid droplets 72 and the aerosol 73 of the reaction solution by the wall 53 and reducing contamination to adjacent samples for nucleic acid extraction.

As illustrated in FIG. 27, the reaction container 2 may have a protection wall to the outside of the reaction portion, which is connected to the bottom of the reaction container to a position higher than the opening end of the reaction portion. The shape of the reaction container 2 provides an effect of shielding dropping of the liquid droplets 72 between the reaction portions and scattering of the aerosol 73 of the reaction solution which may possibly occur upon movement of the magnetic body cover 51 between the reaction portions, reducing contamination to adjacent samples for nucleic acid extraction and samples for nucleic acid extraction at or after the next processing.

Further, as illustrated in FIG. 28, a manufacturer can provide an integral type container 91 of a reaction container 2 and a magnetic body cover 51. The integral type container 91 has fitting portions 92a to 92b for integrating the reaction container 2 and the magnetic body cover 51, and a seal portion 93 for sealing the reaction portion 21. While FIG. 28 illustrates an example in which the reaction portion 21b and the magnetic body cover 51 fit each other, the reaction portion to which the magnetic body cover 51 is provided is not restricted to such reaction portion 21b. Further, the fitting portion 92 may be different in the number and the shape from those illustrated in FIG. 28.

In the integral type container 91, the integral type container 91 may also be disposed such that the opening of the magnetic body cover 51 is equal with the central distance at the apical ends of the plurality of nozzles 31.

The effect of providing the reaction container 2 and the magnetic body cover 51 as the integral type container 91 includes improvement of the simplicity of users' operation due to the reduction for the number of consumption parts to be used and reduction of contamination by sealing the reaction container 2 upon discarding.

While FIG. 7 and FIG. 28 illustrate an example in which each of the reaction portions 21*a* to 21*d* has a circular cross section, the cross section of the reaction portions 21*a* to 21*d* may also be a polygonal or an elliptic shape. The elliptic shape provides an effect of increasing the moving distance in the Y-axis direction upon retaining the magnetic body cover 51 to the cover removing mechanism 23.

Further, the reaction container mounting stand 11 has a cover retaining portion 61 above the open end in the plurality of reaction portions 21*a* to 21*d* for retaining the magnetic body cover 51 mounted on the nozzle mechanism 9.

Figure 9:
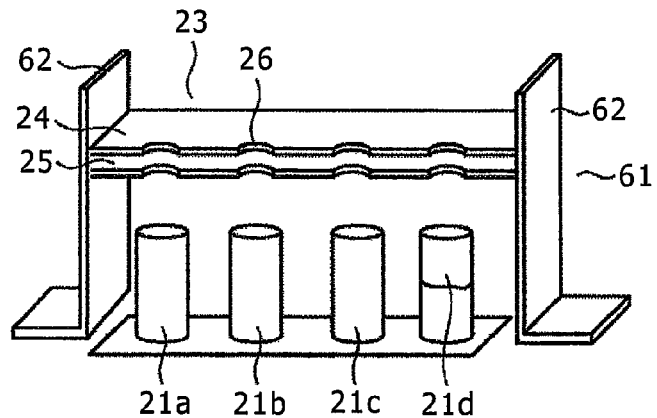
FIG. 9 is a perspective view schematically illustrating a magnetic cover removing mechanism and a reaction container.
Figure 10:
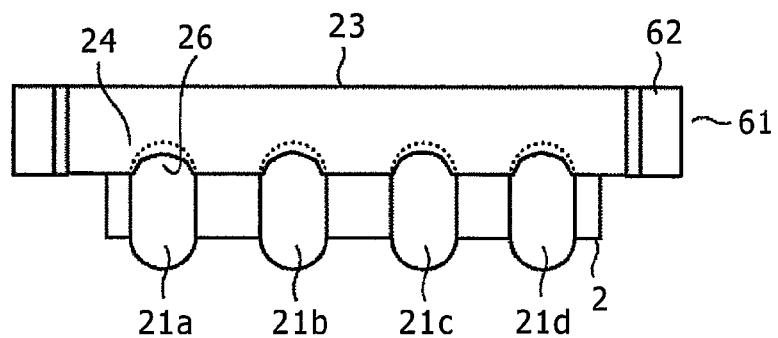
FIG. 10 is an upper plan view schematically illustrating the magnetic cover removing mechanism and the reaction container.

The cover retaining portion 61 provided in the reaction container mounting stand 11 has a cover removing mechanism 23. As illustrated in FIG. 9, the cover removing mechanism 23 has a pair of lateral sides 62 of an L-cross sectional shape and an upper retainer plate 24 and a lower retainer plate 25 situated at a predetermined height by the pair of the lateral sides 62 for holding the magnetic body cover. The upper retainer plate 24 and the lower retainer plate 25 are disposed substantially parallel to each other at a predetermined distance. Further, the upper retainer plate 24 and the lower retainer plate 25 have recesses 26 each of a shape conforming to the outer profile size of the magnetic body cover opposing to a plurality of reaction portions 21*a* to 21*d* respectively. The recess 26 is formed such that the end face is situated at a position facing the inside of the opening of the reaction portions 21*a* to 21*d* when the reaction container 2 is seen from above. FIG. 10 illustrates a plan view of the reaction container and the cover holding portion.

The nucleic acid extractor has a plurality of cover retaining portions 61 corresponding to respective reaction containers 2 when the plurality of the reaction containers 2 are provided.

Figure 12:
FIG. 12 is a plan view of a disposable tip.

Further, the cover retaining portion 61 may also be configured such that the cover removing mechanism 23 can be moved and positioned in the vertical direction (Z-axis direction illustrated in FIG. 12). In this case, a plurality of concave grooves can be formed in parallel in the vertical direction to the surfaces of a pair of sides 62 opposing each other and the cover removing mechanism 23 can be moved vertically along the concave grooves. In this case, fixing means such as pins are preferably disposed so as to fix the cover removing mechanism 23 to the pair of the lateral sides 62.

Figure 11:
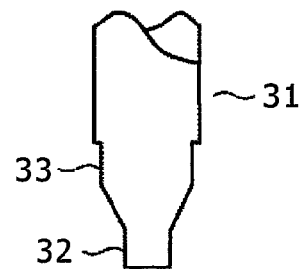
FIG. 11 is a plan view of a nozzle.

In the nucleic acid extractor, the nozzle mechanism 9 has one or a plurality of nozzles 31 as illustrated in FIG. 11. The nozzle mechanism 9 has nozzles 31 at least by the number more than that of the reaction containers 2. In other words, in the nucleic acid extractor, the reaction containers 2 can be disposed by a number less than that of the nozzles 31. More specifically, the nozzles 31 can be provided in parallel, for example, by about 8 to 12 series. By arranging the nozzles 31 in parallel, the processing capacity per unit time (throughput) can be improved.

Although not illustrated, the nozzle 31 has a cylindrical inside, which is connected to a suction/discharge driving device such as a pump device. The nozzle 31 has an apical end 32 of the minimum diameter and an intermediate region 33 diametrically larger than the apical end 32.

Figure 13:
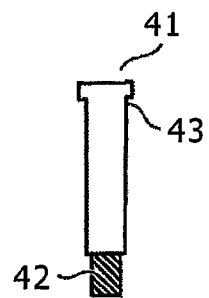
FIG. 13 is a plan view of a magnetic rod.

A disposable tip 35 illustrated in FIG. 12 or a magnetic rod 41 illustrated in FIG. 13 can be mounted selectively to the apical end 32 of the nozzle 31. The inner diameter at the base end of each of the disposable tip 35 and the magnetic rod 41 is substantially made diametrically identical with the apical end 32 of the nozzle 31 and tapered so as to be diametrically decreased toward the apical end. Accordingly, the disposable tip 35 and the magnetic rod 41 can be fit to the nozzle 31 by inserting the apical end 32 of the nozzle 31 from the base end.

Further, the disposable chip 35 has flange 36 at the base end. The magnetic rod 41 has a magnet 42 at the apical end and a fringe 43 at the base end.

A magnetic body cover 51 illustrated in FIG. 1 can be mounted on a middle region 33 of the nozzle 31. In the magnetic body cover 51, the inner diameter of the base end of the magnet cover is substantially identical with that of the middle region 33 of the nozzle 31, and it is also shaped so as to be reduced diametrically toward the apical end. Thus, the magnetic body cover 51 can be fitted to the nozzle 31 by inserting the middle region of the nozzle 31 from the base end. The magnetic body cover 51 has a flange 55 at the base end.

The disposable tip 35 and the magnetic rod 41 (region excluding the magnet 42) can be prepared by using a resin such as polyethylene, polypropylene, or polycarbonate.

Although not illustrated, the nozzle mechanism 9 preferably has a release mechanism for releasing the disposable tip 35, the magnetic rod 41, and the magnetic body cover 51 mounted on the apical end 32 and the middle region 33. For example, a pressing portion that downwardly pushes the flange 36 of the disposable tip 35, the flange 43 of the magnetic rod 41, and the flange 55 of the magnetic body cover 51 can be used as the release mechanisms.

In the nucleic acid extractor, the reagent rack 3 has box-like shape capable of accommodating a plurality of reagent bottles. The reagent rack 3 can accommodate different reagent bottles depending on the specific type of processing implemented on biological samples. For example, when processing of extracting nucleic acid components from biological samples is performed, the reagent rack 3 can accommodate a reagent bottle of a solution containing a chaotropic agent, a reagent bottle of a cleaning solution, a reagent bottle of an eluent, etc. Also, the reagent rack 3 may contain reagent bottles of an identical type by the number identical with that of a plurality of nozzles 31 provided in the nozzle mechanism 9. In this case, the reagent bottles of the identical type are arranged so as to conform to the pitch of the plurality of nozzles 31.

In the nucleic acid extractor, the analyte rack 4 has a box-like shape capable of accommodating a plurality of analyte tubes filled with different or identical biological samples. In the analyte rack 4, a plurality of analyte tubes are arranged so as to conform to the pitch of the plurality of nozzles 31.

In the nucleic acid extractor, the magnetic rod rack 5 has a plurality of openings for accommodating a plurality of magnetic rods 41 illustrated in FIG. 13. The diameter of the opening is somewhat larger than the outer diameter of the magnetic rod 41 and somewhat smaller than that of the flange 43. Such a plurality of openings are arranged so as to conform to the pitch of the plurality of nozzles 31. Specifically, a plurality of openings are juxtaposed by the number identical with or in a multiple of that of the nozzles such that the center pitch of the plurality of openings is approximately equal to the center pitch of the apical ends of the plurality of nozzles 31, and the rows of the openings are formed for a plurality of stages.

In the nucleic acid extractor, the cover rack 6 has a plurality of openings for accommodating a plurality of magnetic body covers 51 illustrated in FIG. 1. The diameter of the opening is somewhat larger than the outer diameter of the magnetic body cover 51 and somewhat smaller than that of the flange 55. Such a plurality of openings are arranged so as to conform to the pitch of the plurality of nozzles 31. Specifically, a plurality of openings are juxtaposed by the number identical with or in a multiple of that of nozzles such that the center pitch of the plurality of the openings is approximately equal to the center pitch of the apical ends of the plurality of the nozzles 31, and the rows of the openings are formed for a plurality of stages.

In the nucleic acid extractor, the tip rack 7 has a plurality of openings for accommodating the plurality of disposable tips 35 illustrated in FIG. 12. The diameter of the opening is somewhat larger than the outer diameter of the disposable tip 35 and somewhat smaller than that of the flange 36. Such plurality of openings are arranged so as to conform to the pitch of the plurality of nozzles 31. Specifically, a plurality of openings are juxtaposed by the number identical with or in a multiple of that of the nozzles such that the center pitch of the plurality of t openings is approximately equal to the center pitch of the apical ends of the plurality of nozzles 31, and the rows of the opening are formed for a plurality of stages.

In the nucleic acid extractor, the waste container 8 is a container for discarding used disposable tip 35, magnetic rod 41, and magnetic body cover 51, and biological samples after processing, cleaning solution, etc., and has a box-like shape. Although not illustrated, the waste container 8 preferably has a release mechanism for releasing the disposable tip 35 and the magnetic body cover 51 mounted on the apical end 32 or the middle region 33 of the nozzle 31. For example, a pressing plate that abuts against the flange 36 of the disposable tip 35 and the flange 55 of the magnetic body cover 51 and drives the nozzle 31 upward thereby pressing the flanges 36 and 55 downward can be used as the release mechanism. It may suffice that the release mechanism is provided either in the nozzle mechanism 9 or in the waste container 8.

Although not illustrated, the drive control device 10 in the nucleic acid extractor has a drive mechanism including a power source such as a motor, a gear mechanism that transmits a power supplied from the power source, an arm, etc., and a control board that outputs a control signal allowing the nozzle mechanism 9 to move along the X-axis, the Y-axis, and the Z-axis and to rotate around the Z-axis illustrated in FIG. 12, to the drive mechanism. Various conditions set by an operator through a not illustrated computer are inputted to the control board.

The nucleic acid extractor thus constructed can perform various types of processing on biological samples. The nucleic acid extractor is to be described below with reference to an embodiment implementing the processing of extracting nucleic acid components from biological samples as an example. Specifically, the nucleic acid extractor performs nucleic acid extraction of mixing silica-coated magnetic beads with a sample containing nucleic acids and other impurities in the presence of a chaotropic agent, allowing nucleic acids to adsorb to the surface of the magnetic beads, separating the magnetic beads that have adsorbed nucleic acids, cleaning them, and eluting nucleic acids from the magnetic beads.

Figure 24:
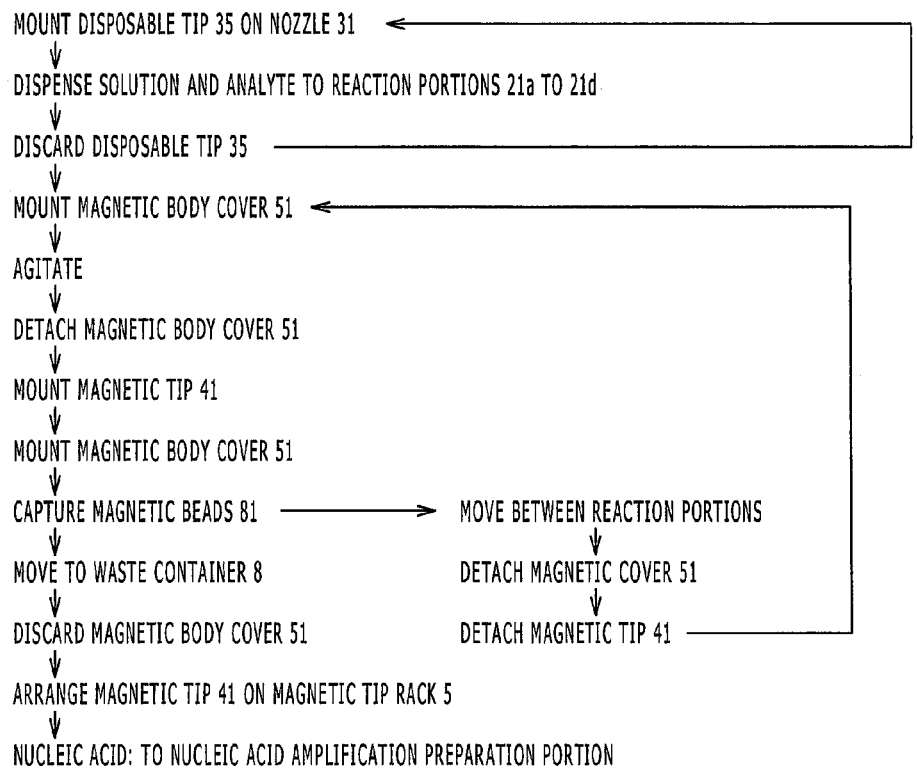
FIG. 24 is a flow chart for the operation of implementing the procedure of a nucleic acid extractor.

The processing performed in the nucleic acid extractor is illustrated as an operation flow chart in FIG. 24. When all of solutions and analytes have been dispensed, the process proceeds from a step of discarding the disposable tip 35 to a step of mounting the magnetic body cover 51. In a case where a reaction portion is not present in the moving destination, a flow goes from the step of capturing the magnetic beads 81 to the step moving to the waste container 8.

Figure 14:
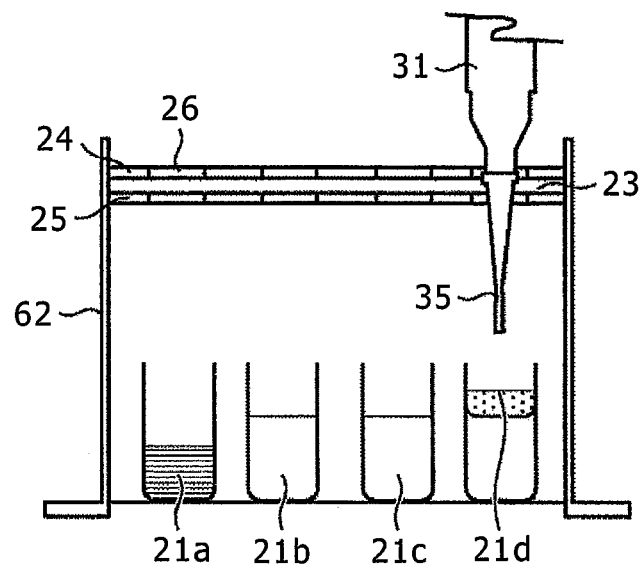
FIG. 14 is a cross-sectional view of a reaction container showing a step of dispensing various liquids to a reaction container in the nucleic acid extracting method according to the present invention.

More specifically, firstly as illustrated in FIG. 14, a solution containing biological samples as a target of processing, a chaotropic agent, and a surfactant is dispensed into the reaction portion 21a, a cleaning solution is dispensed into the reaction portions 21b and 21c, and an eluent is dispensed into the reaction portion 21d. When such solutions are dispensed into the reaction portions 21a to 21d, the disposable tip 35 is mounted on the nozzle 31 of the nozzle mechanism 9. For mounting the disposable tip 35 on the nozzle 31, the drive control device 10 first controls the nozzle mechanism 9 to move to a position at which the center of the base end of the disposable tip 35 accommodated in the tip rack 7 is precisely opposed to the apical end 32 of the nozzle 31 (movement in X-axis and Y-axis directions). Subsequently, the drive control device 10 controls the nozzle mechanism 9 to move downward (Z-axis), by which the disposable tip 35 can be mounted on the apical end 32 of the nozzle 31. Through the series of operations described above, the disposable tips 35 can be mounted on all of the plurality of nozzles 31 of the nozzle mechanism 9.

Then, in a state of mounting the disposable tip 35, the drive control device 10 controls the nozzle mechanism 9 to move to a position above the reagent rack 3, insert the apical end of the disposable tip 35 into the reagent bottle, and suck a given amount of a solution by a not illustrated suction/discharge driving device such as pump means. In this case, when given reagent bottles are provided by the number identical with that of the nozzles 31 and juxtaposed in the reagent rack, the solution can be sucked simultaneously into all of the plurality of disposable tips 35.

Subsequently, the drive control device 10 controls the nozzle mechanism 9 to move to a position above the reaction container 2, and positions the apical ends of the disposable tips 35 above the given reaction portions 21a to 21d. The suction/discharge drive device is actuated in this state, and the solutions sucked in the disposable tips 35 can be dispensed into given reaction portions 21a to 21d. When dispensing of the solutions has been completed, the drive control device 10 controls the nozzle mechanism 9 to move to a position above the waste container 8, and actuates a release mechanism mounted on the nozzle mechanism 9 or the waste container 8, to discard the used disposable tips 35.

The sequential operations described above are in common when a cleaning solution, an eluent, and a solution containing a chaotropic agent and a surfactant are dispensed. Biological samples are dispensed by the sequential operations described above, except that given amounts of biological samples are sucked through analyte tubes accommodated in the analyte rack 4. When the cleaning solution, the eluent, and the solution containing the biological samples, the chaotropic agent, and the surfactant are dispensed, different disposable tips 53 are used respectively.

Figure 15:
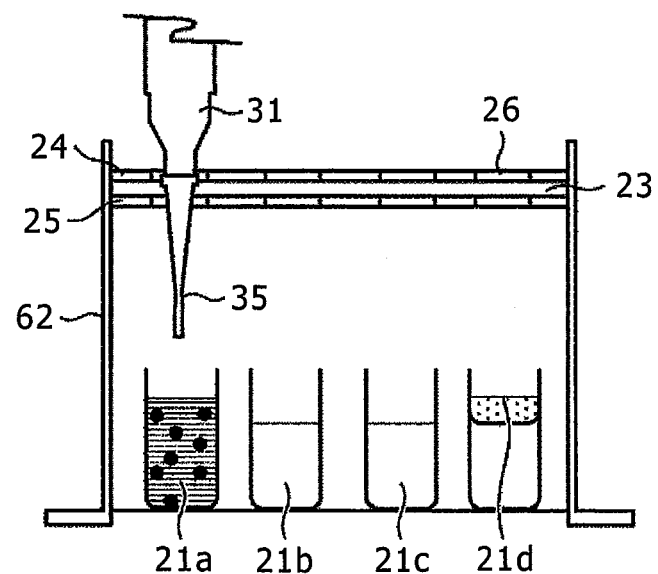
FIG. 15 is a cross-sectional view of the reaction container illustrating a step of dispensing magnetic beads to a reaction container in the nucleic acid extracting method according to the present invention.

Then, as illustrated in FIG. 15, silica-coated magnetic beads 81 are dispensed to the reaction portion 21a to which biological samples as a target of the processing have been dispensed. The magnetic beads 81 may be previously dispensed to the reaction portion 21a, or a solution in which the magnetic beads are dispersed may be dispensed into the reaction portion 21a in the same manner as in the operation of the nozzle mechanism 9 described above. While the biological samples are dispensed in the stage illustrated in FIG. 14, the biological samples may also be dispensed concurrently with the magnetic beads 81, or sequentially in this stage.

Further, a user or a manufacturer of the nucleic acid extractor can previously fill a necessary reagent or a cleaning solution into a plurality of reaction portions in the reaction container. In this case, a portion or the entirety of the reagent rack 3 is sometimes unnecessary.

Beads of any material, shape, and particle diameter can be used as the magnetic beads 81, provided that the beads have features of the magnetic body used so far, for example, in the field of biotechnology. When nucleic acid extraction is performed by the nucleic acid extractor, magnetic beads 81 having the capacity for nucleic acid adsorption are used. The capacity for nucleic acid adsorption can be imparted by coating magnetic bead surfaces with silica.

Since the chaotropic agent is present in the reaction portion 21a in this stage, nucleic acid components contained in the biological samples are adsorbed onto the surfaces of the silica-coated magnetic beads 81. In this stage, the content inside the reaction portion 21a may be agitated. The content inside the reaction portion 21a can be agitated, for example, by a method of periodically applying a magnetic field from the outside of the reaction container 2 to allow the magnetic beads 31 to move in the inside, or a method of mounting the disposable tip 35 and the magnetic body cover 51 on the nozzle 31 and controlling the nozzle mechanism 9 by the drive control device 10 to allow the disposable tip 35 and the magnetic body cover 51 mounted on the nozzle 31 to rotate or shake in the inside of the reaction portion 21a.

Figure 16:
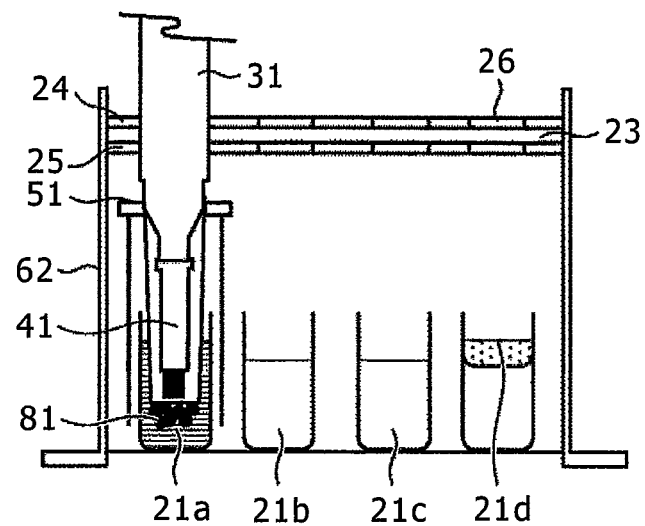
FIG. 16 is a cross-sectional view of the reaction container illustrating a step of capturing magnetic beads in the nucleic acid extraction method according to the present invention.

Then, as illustrated in FIG. 16, the magnetic rod 41 and the magnetic body cover 51 are mounted on the nozzle 31 to capture the magnetic beads 81 in the reaction portion 21a on the apical end of the magnetic body cover 51. In this stage, the magnetic rod 41 and the magnetic body cover 51 are mounted on the nozzle 31 in the same manner as in the operation of mounting the disposable tip 35 on the nozzle 31 by controlling the nozzle mechanism 9 by the drive control device 10 described above. The magnetic body cover 51 is mounted on the middle region 33 of the nozzle 31 after the magnetic rod 41 has been mounted on the apical end 32 of the nozzle 31. In this stage, magnetic beads 81 can be securely captured at the apical end of the magnetic body cover 51 by allowing the apical ends of the magnetic rod 41 and the magnetic body cover 51 to rotate, shake, or move vertically inside the reaction portion 21a. The apical ends of the magnetic rod 41 and the magnetic body cover 51 can be rotated, shaken, or moved vertically inside the reaction portion 21a by controlling the nozzle mechanism 9 by the drive control device 10.

Figure 17:
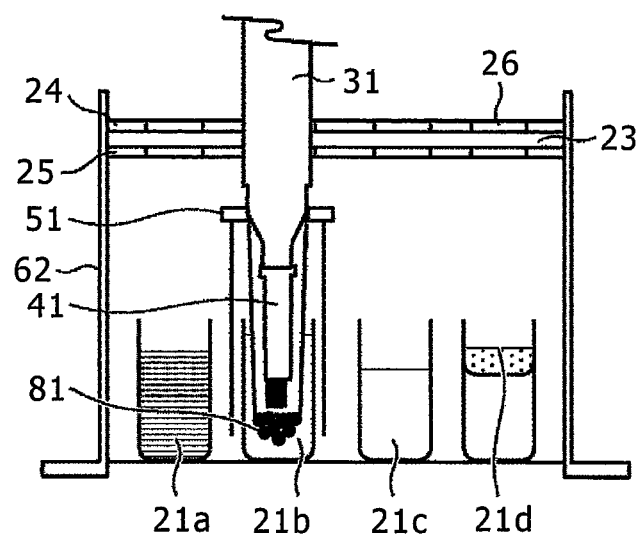
FIG. 17 is a cross-sectional view of the reaction container illustrating a step of transporting magnetic beads in the nucleic acid extraction method according to the present invention.

Then, as illustrated in FIG. 17, the drive control device 10 drive controls the nozzle mechanism 9 to move the apical ends of the magnetic rod 41 and the magnetic body cover 51 from the reaction portion 21a to the reaction portion 21b with the magnetic beads 81 being captured. In this case, the magnetic rod 41 and the magnetic body cover 51 are moved with scarce space above the reaction container 2 in order to suppress cross contamination as less as possible.

Figure 18:
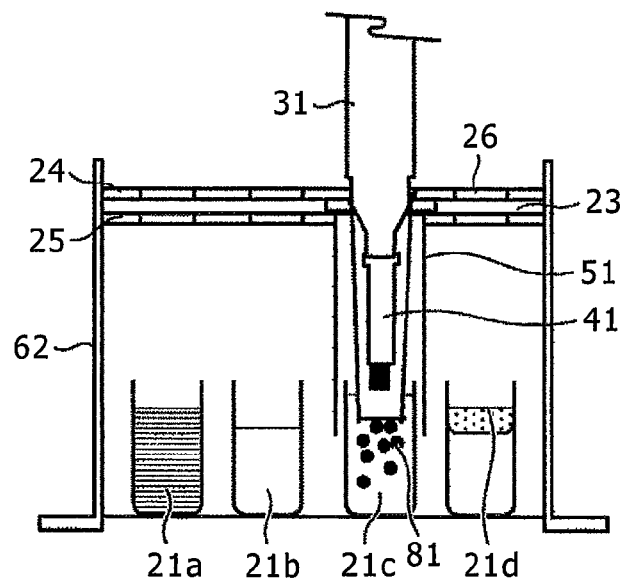
FIG. 18 is a cross-sectional view of the reaction container illustrating a step of removing the magnetic beads captured by the nucleic acid extraction method according to the present invention.
Figure 19:
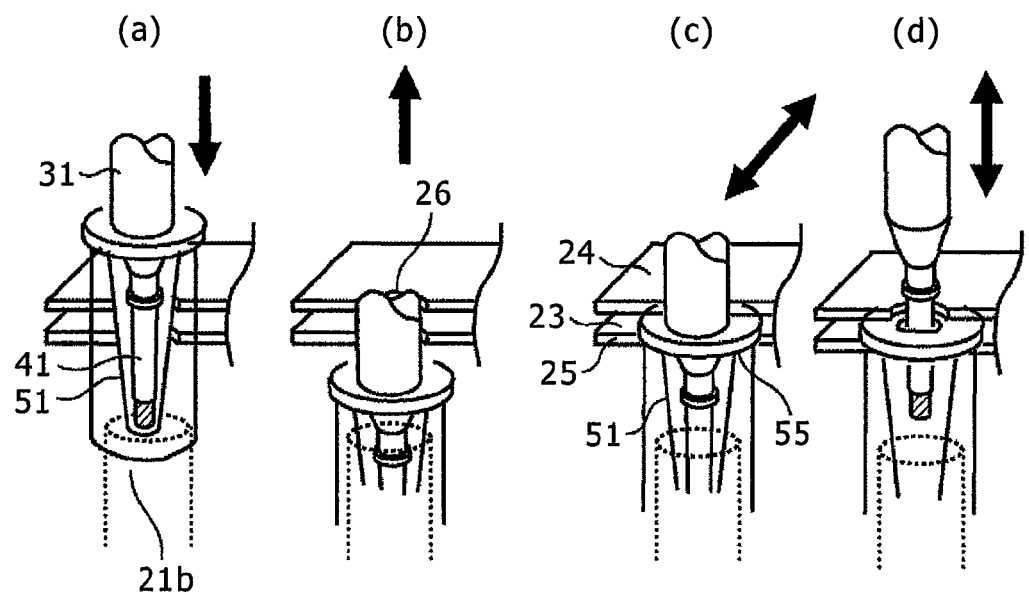
FIG. 19 is a perspective view for a main portion illustrating a nozzle and a cover-removing mechanism in a step of detaching the magnetic beads captured in the nucleic acid extraction method according to the present invention.

Subsequently, as illustrated in FIG. 18, the drive control device 10 drive controls the nozzle mechanism 9 to detach the magnetic beads 81 from the apical end of the magnetic body cover 51 by utilizing a cover removing mechanism 23.

FIG. 19(a) to (d) illustrate the operation from the step of inserting the magnetic body cover 51 into the reaction portion 21b with the magnetic beads 81 being captured to the operation of detaching the magnetic beads 81 from the apical end of the magnetic body cover 51.

First, as illustrated in FIG. 19(a), the drive control device 10 drives to control the nozzle mechanism 9 to insert the apical end of the nozzle 31 mounted with the magnetic rod 41 and the magnetic body cover 51 into the reaction portion 21b (downward direction in Z-axis).

Subsequently, as illustrated in FIG. 19(b), the apical end of the nozzle 31 on which the magnetic rod 41 and the magnetic body cover 51 have been mounted is lifted from the inside of the reaction portion 21b (upward direction in Z-axis).

Then, as illustrated in FIG. 19(c), the nozzle 31 is lifted till the flange 55 of the magnetic body cover 51 reaches a position between the upper retainer plate 24 and the lower retainer plate 25 of the cover-removing mechanism 23, and then allowed to move so as to fir the magnetic body cover 51 fits into the recess 26 (Y-axis). This movement causes the flange 55 of the magnetic body cover 51 to be inserted and retained between the upper retainer plate 24 and the lower retainer plate 25. The recess 26 is formed in such a manner that the end face thereof is situated to a position facing the inside of the opening of each of the reaction portions 21a to 21d when the reaction container 2 is seen from above. Accordingly, the magnetic body cover 51 can be securely fit into the recess 26 without contact of the periphery of the magnetic cover 51 to the lateral side of the reaction portion 21b in the operation of fitting the magnetic body cover 51 to the recess 26.

Subsequently, as illustrated in FIG. 19(d), the drive control device 10 drive controls the nozzle mechanism 9 to further lift the nozzle 31 (upward in Z-axis direction). By the lifting operation, the upper surface of the flange 55 of the magnetic body cover 51 mounted on the nozzle 31 is retained by the upper retainer plate 24, and only the magnetic body cover 51 is separated from the nozzle 31. Since the magnetic rod 41 mounted on the nozzle 31 is lifted upward together with the nozzle 31, magnetic beads 81 captured at the apical end of the magnetic body cover 51 are detached from the apical end, and settled to the bottom of the reaction portion 21b (FIG. 18). By the use of the cover removing mechanism 23, the magnetic body cover 51 can be removed from the nozzle 31 and the magnetic body cover 51 can be retained in a state where the apical end of the magnetic body cover 51 is inserted in the reaction portions 21a to 21d.

Figure 25:
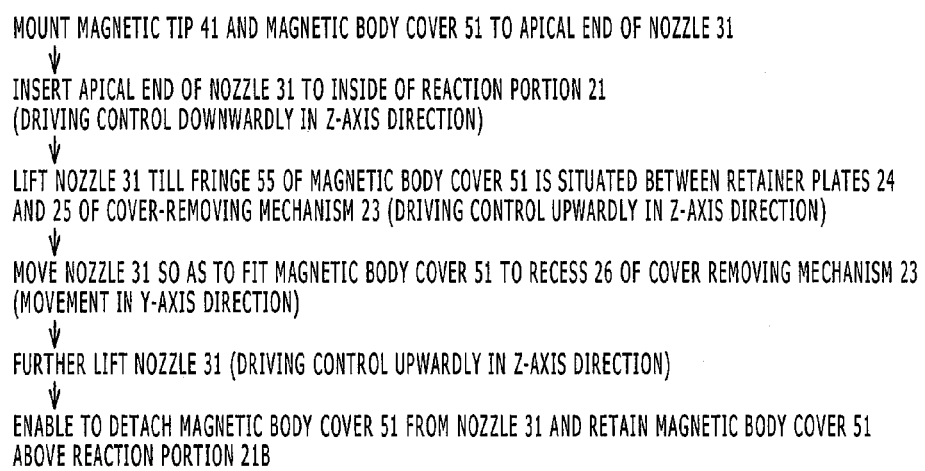
FIG. 25 is a flow chart for the operation of detaching a magnetic body cover from a nozzle.

FIG. 25 illustrates the state of processing upon removing the magnetic body cover 51 from the nozzle 31 by the driving control of the drive control device 10 as a flow chart of operation.

By retaining the apical end of the magnet cover 52 of the magnetic body cover 51 in a state being inserted into each of the reaction portions 21a to 21d, dropping of the liquid and the magnetic beads 81 and scattering of the aerosol can be reduced and contamination to the adjacent samples for nucleic acid extraction can be reduced.

As described above, the magnetic beads 81 in the reaction portion 21a can be moved to the reaction portion 21b by merely drive controlling the nozzle mechanism 9 by the drive control device 10. The operation does not need a step of drawing out a solution from the reaction portion 21a and the magnetic beads 81 can be moved extremely conveniently.

The magnetic beads 81 can be cleaned by a cleaning solution dispensed into the reaction portion 21b, and impurities such as proteins derived from biological samples can be removed from the surfaces of the magnetic beads 81 in the state illustrated in FIG. 18. In this stage, the cleaning solution in the reaction portion 21b may be agitated in order to further enhance the cleaning efficiency. The content of the reaction portion 21b can be agitated by using, for example, a method of applying a magnetic field periodically from the outside of the reaction container 2 thereby allowing the magnetic beads 81 to move in the inside, or a method of detaching the magnetic rod 41 mounted on the nozzle 31, then, mounting moving the magnetic body cover 51 retained on the cover removing mechanism 23 on the nozzle 31 again thereby allowing the magnetic body cover 51 to rotate or shake inside the reaction portion 21b. The operation of mounting the magnetic body cover 51 on the nozzle 31 can be carried out by reversing the sequential operations illustrated in FIGS. 19(a) to (d).

FIG. 26 illustrates the processing performed when mounting the magnetic body cover 51 on the nozzle 31 by driving control of the drive control device 10 as a flow chart of operation.

Figure 20:
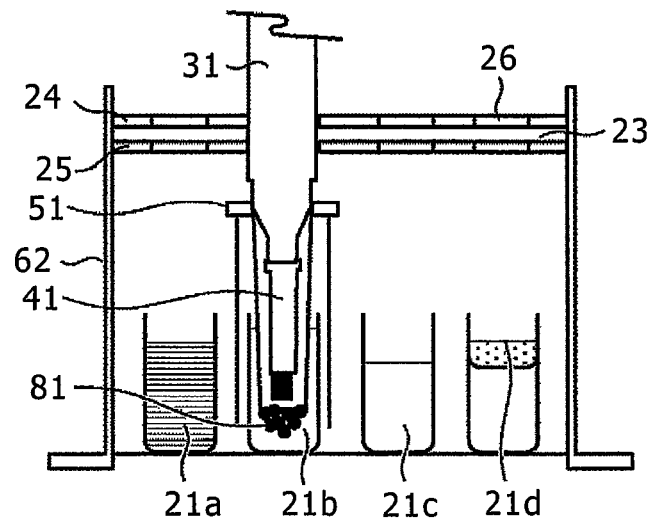
FIG. 20 is a cross-sectional view of a reaction container in a step of capturing magnetic beads in the nucleic acid extraction according to the present invention.

Subsequently, as illustrated in FIG. 20, the magnetic beads 81 cleaned in the reaction portion 21b are captured again at the apical end of the magnetic body cover 51. This stage can be carried out by controlling to drive the nozzle mechanism 9 by the drive control device 10, in the same manner as in the stage illustrated in FIG. 16.

Figure 21:
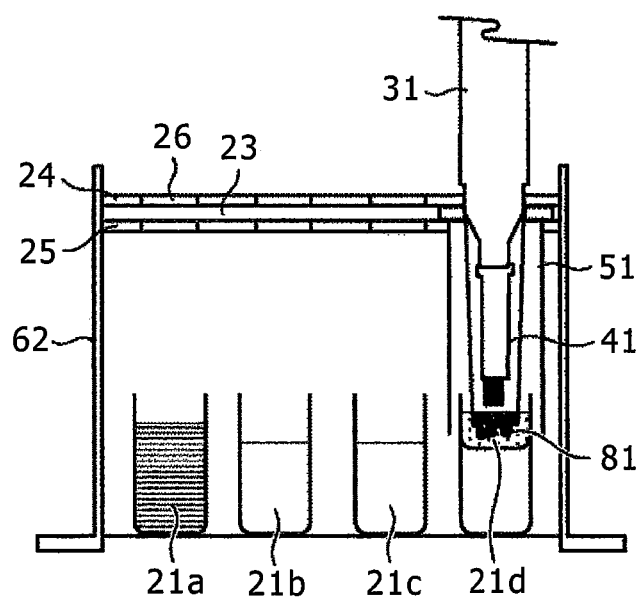
FIG. 21 is a cross-sectional view of the reaction container illustrating a step of moving the magnetic beads into an eluent in the nucleic acid extraction method according to the present invention.

Subsequently, the magnetic beads 81 captured at the apical end of the magnetic body cover 51 are subjected to second cleaning in the reaction portion 21c (not illustrated) and, as illustrated in FIG. 21, the magnetic beads 81 captured at the apical end of the magnetic body cover 51 are moved to the reaction portion 21d into which the eluent has been dispensed. This stage can be carried out by drive controlling the nozzle mechanism 9 by the drive control device 10 in the same manner as in the stage illustrated in FIG. 17.

Figure 22:
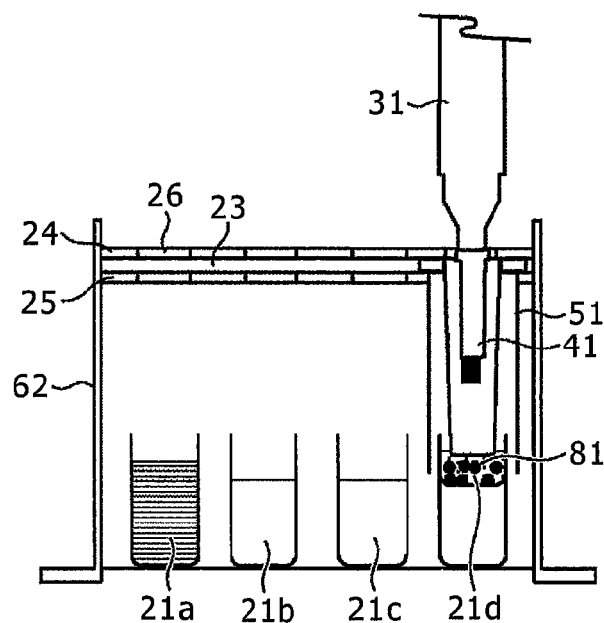
FIG. 22 is a cross-sectional view of the reaction container illustrating a step of dipping the magnetic beads in the nucleic acid extraction method according to the present invention.

Subsequently, as illustrated in FIG. 22, the drive control device 10 drive controls the nozzle mechanism 9 to detach the magnetic beads 81 from the apical end of the magnetic body cover 51 by utilizing the cover removing mechanism 23. The stage can be carried out by drive controlling the nozzle mechanism 9 by the drive control device 10 in the same manner as in the stage illustrated in FIG. 19. In this stage, nucleic acid components adsorbed to the surface of the magnetic beads 81 can be eluted in the elute.

Figure 23:
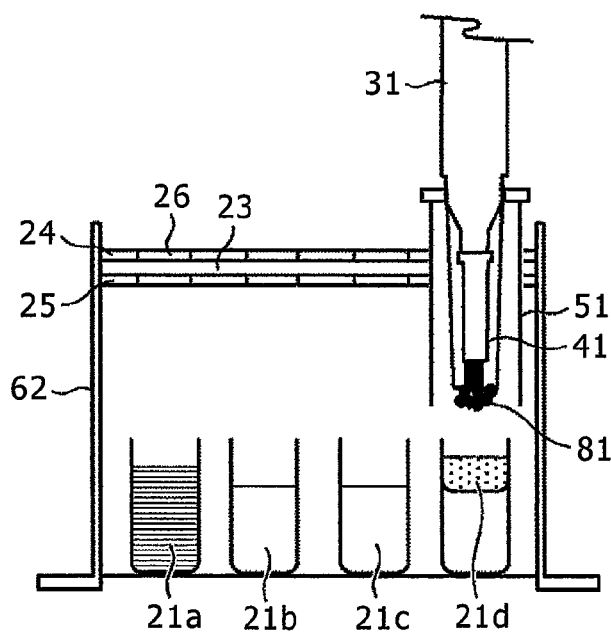
FIG. 23 is a cross-sectional view of the reaction container illustrating a step of recovering the magnetic beads in an eluent in the nucleic acid extraction method according to the present invention.

Finally, as illustrated in FIG. 23, the magnetic beads 81 and 40 in the elute are captured again at the apical end of the magnetic body cover 51 in the same manner as in the state illustrated in FIG. 20. Then, the drive control device 10 controls the nozzle mechanism 9 to move to a position above the waste container 8 and actuates the removing mechanism mounted on the nozzle mechanism 9 or the waste container 8 to discard the magnetic body cover 51 in a state of capturing the magnetic beads 81 at the apical end.

Then, the drive control device 10 controls the nozzle mechanism 9 to move to a position above the magnetic rod rack 5, actuates the removing-mechanism mounted to the nozzle mechanism 9, to accommodate the magnetic rod 41 mounted on the nozzle 31 in the magnetic rod rack 5. The magnetic rod 41 accommodated in the magnetic rod rack 5 is usable repetitively for different analytes and the processing cost per analyte can be decreased.

Figure 29:
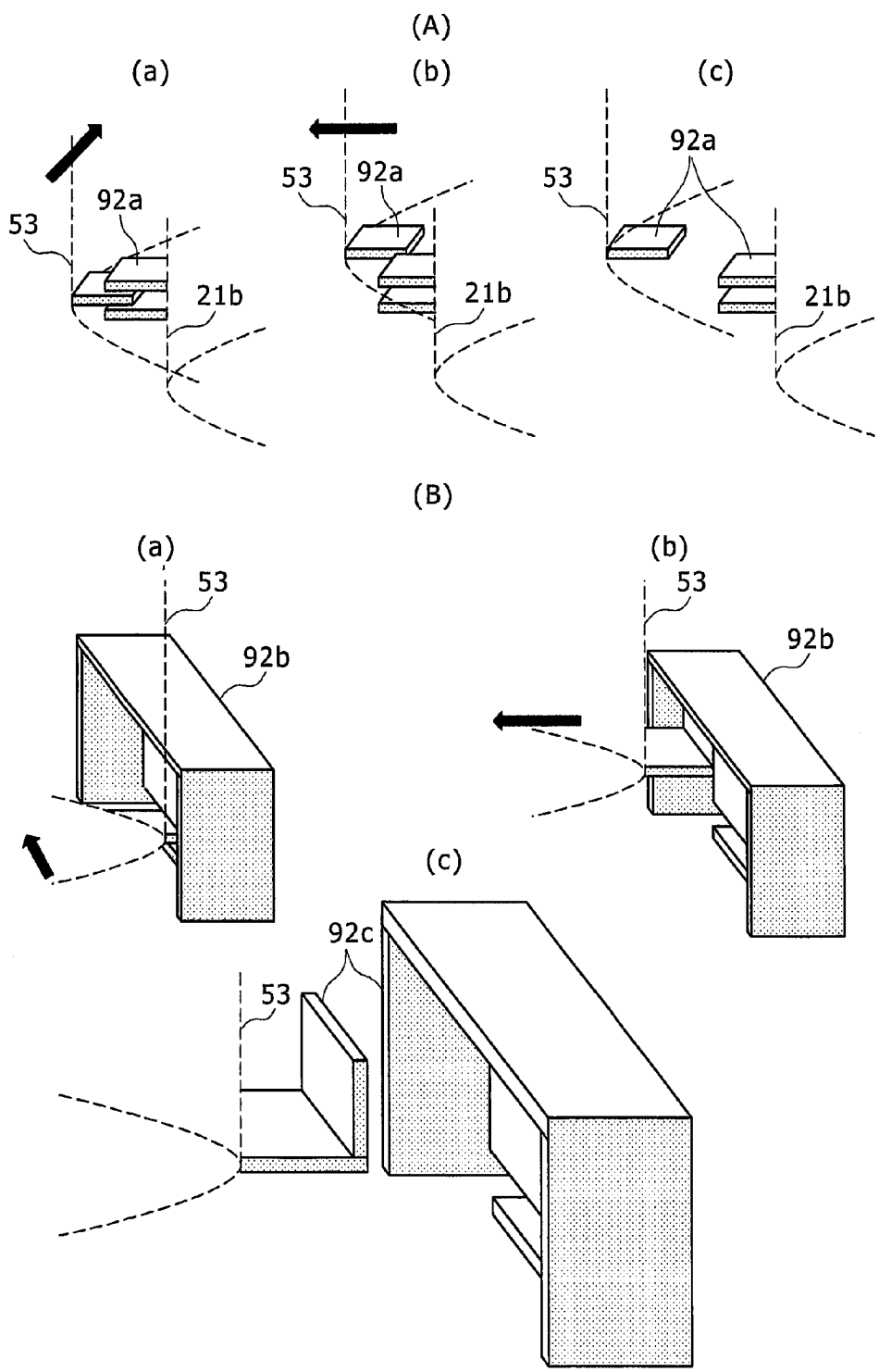
FIG. 29 is a perspective view illustrating a fitting portion in a step of separating the integral type container into a reaction container and a magnetic body cover.

When the integral type container 91 is used, the magnetic body cover 51 and the reaction container 2 are separated before dispensing a solution to the reaction container 2. Specifically, the drive control device 10 controls the nozzle mechanism 9 to move to a position at which the center of the opening of the magnetic body cover 51 of the integral type 91 accommodated in the cover rack 6 and the apical end 32 of the nozzle 31 oppose precisely (movement in X-axis and Y-axis directions). Then, the drive control device 10 controls the nozzle mechanism 9 to move downward (Z-axis), by which the integral type container 91 can be mounted on the apical end 32 of the nozzle 31. Then, in a state where the integral container 91 is mounted, the drive control device 10 controls the nozzle mechanism 9 to move to a position above the reaction container mounting stand 11 and the nozzle mechanism 9 to move downward (Z-axis), thereby disposing the integral type container 91 to the reaction container mounting stand 11. Subsequently, the drive control device 10 controls the nozzle mechanism 9 to move in the directions of the X-axis and the Y-axis in a state where the integral type container 91 is mounted as it is to the apical end 32 of the nozzle 31, thereby releasing fitting between the reaction container 2 and the magnetic body cover 51. Then, the nozzle mechanism 9 is moved upward (Z-axis) in a state where the magnetic body cover 51 is mounted as it is on the apical end 32 of the nozzle 31, thereby separating the magnetic body cover 51 from the reaction container 2. FIGS. 29(A) and (B) illustrate the sequential operation of releasing fitting between the reaction container 2 and the magnetic body cover 51. FIG. 30 illustrates the processing of separating the magnetic body cover 51 from the integral type container 91 by driving control of the drive control device 10 as a flow chart of operation.

The method of separating the integral type container 91 into the reaction container 2 and the magnetic body cover 51 is not restricted to the method of releasing the fitting. Further, the method of releasing the fitting is not restricted to the method of moving the nozzle mechanism 9 in the directions of the X-axis and the Y-axis by the control of the drive control device 10, but a method of moving the nozzle mechanism 9 only in mono-axial direction or tri-axial direction is also possible.

When the integral type container 91 is used, it is also possible to capture the magnetic beads 81 in the elute at the apical end of the magnetic body cover 51 and, subsequently, seal the reaction portion 21. Specifically, the drive control device 10 drives to control the nozzle mechanism 9 to move the nozzle 31 to which the magnetic body cover 51 having magnetic beads 81 captured at the apical end is moved to a position above the reaction portion 21a. Then, the drive control device 10 controls the nozzle mechanism 9 to move downward (Z-axis) by which the seal portion 93 of the magnetic body cover 51 is inserted into and seal the opening of the reaction portion 21a. Subsequently, the removing mechanism of the nozzle mechanism 9 is actuated to detach the magnetic body cover 51 from the nozzle 31. FIG. 31 illustrates an integral type container in which the reaction portion 21a is sealed with a magnetic body cover 51.

Sealing of the reaction portion 21a with the magnetic body cover 51 provides an effect of reducing the possibility of diffusion of biological samples with incomplete processing and the nucleic acid components not adsorbed at the surface of the magnetic beads 81 for some reason, and reducing contamination to the samples for nucleic acid extraction at and after the next time.

The reaction portion 21 sealed by the magnetic body cover 51 of the integral type container 91 is not restricted to the reaction portion 21a.

As has been described above, in the nucleic acid extraction method using the nucleic acid extractor, the magnetic beads 81 are captured at the apical end of the magnetic body cover 51 and moved to each of the reaction portions 21a to 21d. In the existent method of sucking the unnecessary solution from the solution containing the magnetic beads 81 by using a tip or discharging the unnecessary solution, since the magnetic beads are sucked together upon sucking the unnecessary solution, there has been a problem that the magnetic beads are lost. However, the nucleic acid extracting method using the nucleic acid extractor described above can realize nucleic acid extracting processing at high extraction efficiency with no problems such as loss of the magnetic beads 81.

As has been described above, the extracted nucleic acids are prepared together with a plurality of reagents for nucleic acid amplification into a reaction solution for nucleic acid amplification in the nucleic acid amplification preparation portion 102 in FIG. 6 and, further, amplification reaction and detection of nucleic acids are performed in the nucleic acid amplification reaction and detection section 103 in FIG. 6.

LIST OF REFERENCE SIGNS

1: mounting stand;
2: reaction container;
3: reagent rack;
4: analyte rack;
5: magnetic rod rack;
6: cover rack;
7: tip rack;
8: waste container;
9: nozzle mechanism;
10: drive control device;
11: reaction container mounting stand;
21a to 21d: reaction portions
23: cover removing mechanism;
24: upper retainer plate;
25: lower retainer plate;
26: recess;
31: nozzle;
32: apical end;
33: middle region;
35: disposable tip;
36, 43, 55: fringe;
41: magnetic rod;
42: magnet
51: magnetic body cover
52: magnet cover
53: wall portion
54: upper portion
61: cover retaining portion
62: lateral side
71: liquid
72: liquid droplet
73: aerosol
81: magnetic beads
101: nucleic acid extractor
102: nucleic acid amplification preparation portion
103: nucleic acid amplification reaction detection portion
91: integral type container
92: fitting portion
93: seal portion

The invention claimed is:

1. An apparatus for nucleic acid extraction using silica-coated magnetic beads under the presence of a chaotropic agent, the apparatus comprising:
   a magnetic body accommodation portion accommodating a magnetic body inside the magnetic body accommodation portion for separating the magnetic body and a reaction container from each other;
   an outer wall covering an outside of the reaction container in a state of accommodating at least a portion of the magnetic body accommodation portion in the reaction container, the outer wall being spaced outwardly from the magnetic body accommodation portion by a space sufficient to accommodate the reaction container between the magnetic body accommodation portion and the outer wall; and
   a lid covering a portion above the reaction container in a state of accommodating at least a portion of the magnetic body accommodating portion in the reaction container;
   wherein the lid extends outwardly from the magnetic body accommodating portion to the outer wall to form a flange extending beyond an outside of the outer wall.

2. The apparatus for nucleic acid extraction according to claim 1,
   wherein a lower end of the outer wall is situated below a lower end of the magnetic body accommodation portion.

3. The apparatus for nucleic acid extraction according to claim 1,
   wherein the magnetic body accommodation portion and the outer wall are connected at upper ends thereof by the lid.

4. The apparatus for nucleic acid extraction according to claim 1,
   wherein the magnetic body accommodation portion has a circular cross-sectional shape.

5. The apparatus for nucleic acid extraction according to claim 1,
   wherein the outer wall has a circular cross-sectional shape.

6. The apparatus for nucleic acid extraction according to claim 1,
   wherein the flange of the lid extends sufficiently far beyond the outside of the outer wall to be placed between an upper plate and a lower plate for retaining the apparatus for nucleic acid extraction.

7. A nucleic acid extractor using silica-coated magnetic beads under the presence of a chaotropic agent, comprising:
   an apparatus for nucleic acid extraction having a magnetic body accommodation portion accommodating a magnetic body inside the magnetic body accommodation portion for separating the magnetic body and a reaction container from each other, an outer wall covering an outside of the reaction container in a state of accommodating at least a portion of the magnetic body accommodating portion in the reaction container, the outer wall being spaced outwardly from the magnetic body accommodation portion by a space sufficient to accommodate the reaction container between the magnetic body accommodation portion and the outer wall, and a lid covering a portion above the reaction container in a state of accommodating at least a portion of the magnetic body accommodation portion in the reaction container;
   a magnetic body for capturing the magnetic beads;
   a plurality of said reaction containers; and a transporting portion for transporting the apparatus for nucleic acid extraction from a reaction container to another reaction container;

wherein the lid extends outwardly from the magnetic body accommodating portion to the outer wall to form a flange extending beyond an outside of the outer wall.

8. The nucleic acid extractor according to claim 7, the nucleic acid extractor has a retaining portion fitting the flange and retaining the apparatus for nucleic acid extraction.

9. The nucleic acid extractor according to claim 8, wherein the retaining portion has two plate-like members for putting the flange therebetween.

10. The nucleic acid extractor according to claim 8, wherein the retaining portion has two plates spaced apart for placing the flange therebetween.

11. The nucleic acid extractor according to claim 8, wherein the retaining portion has an upper plate and a lower plate; and wherein the flange of the lid extends sufficiently far beyond the outside of the outer wall to be placed between the upper plate and the lower plate for retaining the apparatus for nucleic acid extraction.

12. The nucleic acid extractor according to claim 7, wherein a lower end of the outer wall is situated below a lower end of the magnetic body accommodation portion.

13. The nucleic acid extractor according to claim 7, wherein the magnetic body accommodation portion and the outer wall are connected at upper ends thereof by the lid.

14. The nucleic acid extractor according to claim 7, wherein the magnetic body accommodation portion has a circular cross-sectional shape.

15. The nucleic acid extractor according to claim 7, wherein the outer wall has a circular cross-sectional shape.

* * * * *